(12) United States Patent
Smedsrud et al.

(10) Patent No.: US 12,072,269 B2
(45) Date of Patent: Aug. 27, 2024

(54) SELF-CONTAINED CALIBRATION APPARATUS FOR GAS SENSOR

(71) Applicant: Rosemount Inc., Shakopee, MN (US)

(72) Inventors: Jacob J. Smedsrud, Blaine, MN (US); Ryan T. Lindsey, Eden Prairie, MN (US); Greg E. Gindele, Maple Lake, MN (US); Todd L. Larson, Shakopee, MN (US); Sean P. McLeskey, Eden Prairie, MN (US)

(73) Assignee: Rosemount Inc., Shakopee, MN (US)

( * ) Notice: Subject to any disclaimer, the term of this patent is extended or adjusted under 35 U.S.C. 154(b) by 672 days.

(21) Appl. No.: 16/369,231

(22) Filed: Mar. 29, 2019

(65) Prior Publication Data
US 2020/0309647 A1    Oct. 1, 2020

(51) Int. Cl.
*G01N 1/22*    (2006.01)
*G01N 33/00*    (2006.01)

(52) U.S. Cl.
CPC ....... *G01N 1/2205* (2013.01); *G01N 33/0006* (2013.01); *G01N 2001/2288* (2013.01)

(58) Field of Classification Search
CPC ............. G01N 1/2205; G01N 33/0006; G01N 2001/2288; G01N 1/2273; G01N 33/0036; G01N 33/0009
USPC .......................................................... 73/1.06
See application file for complete search history.

(56) References Cited

U.S. PATENT DOCUMENTS

| | | | |
|---|---|---|---|
| 4,279,142 A * | 7/1981 | McIntyre | G01N 27/4175 73/1.06 |
| 5,363,690 A | 11/1994 | Evangelista et al. | |
| 5,879,527 A * | 3/1999 | Kiesele | B01D 39/1661 204/431 |
| 5,993,743 A * | 11/1999 | Nordman et al. | G01N 33/0009 422/94 |
| 6,252,510 B1 | 6/2001 | Dungan | |
| 6,670,887 B2 | 12/2003 | Dungan | |
| 6,794,991 B2 | 9/2004 | Dungan | |
| 7,089,778 B2 | 8/2006 | Rabenecker et al. | |
| 7,345,590 B2 | 3/2008 | Nakano et al. | |
| 7,402,284 B2 * | 7/2008 | McGee et al. | G01N 1/2252 422/83 |

(Continued)

FOREIGN PATENT DOCUMENTS

CN    207148066 U  *  3/2018   ............. B01D 46/00
EP    PCT/EP2002/000369 A    7/2002

(Continued)

OTHER PUBLICATIONS

U.S. Appl. No. 15/392,388, filed Dec. 28, 2016, Application and Drawings, 16 pages.

(Continued)

*Primary Examiner* — Marrit Eyassu
(74) *Attorney, Agent, or Firm* — Christopher R. Christenson; Kelly, Holt & Christenson, P.L.L.C.

(57) ABSTRACT

A detachable filter assembly includes a filter, a filter assembly housing defining a body of the filter assembly, an attachment mechanism configured to couple to a sensor installation, a securing mechanism configured to mate with a mating feature on the sensor installation, and a calibration port configured to provide a direct fluid pathway to the sensor installation.

15 Claims, 16 Drawing Sheets

(56) References Cited

U.S. PATENT DOCUMENTS

| | | | |
|---|---|---|---|
| 8,109,148 B2* | 2/2012 | Habibi | G01L 19/0007 73/708 |
| 8,358,105 B2 | 1/2013 | Barten et al. | |
| 2006/0162426 A1* | 7/2006 | Lange | G01N 21/3504 73/31.05 |
| 2006/0266097 A1* | 11/2006 | Eickhoff | G01N 27/4163 73/1.06 |
| 2008/0156071 A1 | 7/2008 | Tobias | |
| 2008/0274401 A1 | 11/2008 | Broy et al. | |
| 2011/0042570 A1 | 2/2011 | Wong | |
| 2011/0239740 A1* | 10/2011 | Fujita | G01N 27/4077 73/31.07 |
| 2012/0297860 A1 | 11/2012 | Izawa et al. | |
| 2012/0313370 A1 | 12/2012 | Pompeii | |
| 2013/0062223 A1 | 3/2013 | Rabbett | |
| 2013/0105009 A1* | 5/2013 | Oda | F01M 13/0011 137/517 |
| 2013/0263854 A1* | 10/2013 | Taylor | A61M 16/0858 128/204.23 |
| 2013/0327005 A1 | 12/2013 | Menssen et al. | |
| 2014/0083852 A1 | 3/2014 | Yamamoto et al. | |
| 2014/0263099 A1 | 9/2014 | Patera et al. | |
| 2014/0295690 A1 | 10/2014 | Pacheco et al. | |
| 2014/0326081 A1* | 11/2014 | Pierry | G01N 1/2247 73/863.23 |
| 2015/0177206 A1 | 6/2015 | Basham et al. | |
| 2015/0204830 A1 | 7/2015 | Arunachalam | |
| 2015/0265860 A1 | 9/2015 | Kennedy et al. | |
| 2015/0369788 A1* | 12/2015 | Andres | B01D 35/31 210/85 |
| 2016/0084729 A1 | 3/2016 | Huseynov et al. | |
| 2016/0213954 A1* | 7/2016 | Ding | B01D 46/0086 |
| 2017/0080261 A1* | 3/2017 | Sutton | A62B 23/02 |
| 2017/0217634 A1 | 8/2017 | Hendrickson et al. | |
| 2017/0254196 A1* | 9/2017 | Campanella | G01N 33/0006 |
| 2017/0276634 A1 | 9/2017 | Saffell et al. | |
| 2018/0015505 A1 | 1/2018 | Stevenson et al. | |
| 2018/0085696 A1* | 3/2018 | Morris | B01D 46/0005 |

FOREIGN PATENT DOCUMENTS

| | | | | |
|---|---|---|---|---|
| GB | 2559704 A | * | 8/2018 | G01N 1/22 |
| JP | 2002022655 A | * | 1/2002 | |
| JP | 2002257773 A | | 9/2002 | |
| JP | 3875164 B2 | * | 1/2007 | |
| JP | 2008070286 A | * | 3/2008 | |
| JP | 2012251812 A | | 12/2012 | |
| KR | 100609510 B1 | * | 8/2006 | |
| RU | 2082956 C1 | | 6/1997 | |
| WO | 2016-030735 A | | 3/2016 | |

OTHER PUBLICATIONS

U.S. Appl. No. 14/449,359, filed Mar. 3, 2017, Application and Drawings, 18 pages.
U.S. Appl. No. 16/369,189, filed Mar. 29, 2019, Application and Drawings, 14 pages.
International Search Report and Written Opinion for International Patent Application No. PCT/US2020/022922, dated Jul. 7, 2020, 13 pages.
Detcon Hydrogen Sulfide Sensor Model DM-700-H2S Product Data Sheet, retrieved from http://www.detcon.com/1-documents/data_sheets/1-sensors/Model%20700/DM-700/Hydrogen%20Sulfide%20DM-700-H2S%20PDS.pdf, retrieved on Aug. 22, 2017, 2 pages.
Det-Tronics Electrochemical Toxic Gas Detector GT3000 Series Specification Data, retrieved from http://www.det-tronics.com/ProductCatalog/GasDetection/Documents/90-1199-10.1-GT3000.pdf, retrieved on Aug. 22, 2017, 2 pages.
First Examination Report dated Mar. 30, 2022, for Indian Patent Application No. 202127043179, 6 pages including English Translation.
Search Report for European Application No. 20783572.9, Dated Oct. 31, 2022, 15 pages.
First Office Action for Japanese Application No. 2021-557895, Dated Oct. 18, 2022, 14 pages.
First Examination Report for Australian Patent Application No. 2020256029, dated Sep. 8, 2022, 3 pages.
First Chinese Office Action dated May 20, 2022, for Chinese Patent Application No. 201911239452.4, 22 pages including English translation.
Canadian Office Action dated Jun. 22, 2022, for Canadian Patent Application No. 3135288, 3 pages.
Second Office Action For Chinese Patent Application No. 201911239452.4, Dated Nov. 24, 2022, 16 pages including English Translation.
Rejection Decision for Chinese Patent App# 201911239452.4. Dated Jun. 30, 2023, 17 pages including English Translation.

* cited by examiner

SELF-CONTAINED CALIBRATION APPARATUS FOR GAS SENSOR

BACKGROUND

The process industry often employs gas sensors in order to detect the presence of a particular gas, often as part of a safety system. This is important as many gases may be harmful to human health and/or the environment. Industrial gas sensors are normally mounted near the process area of a plant or control room, or an area to be protected. Generally, industrial gas sensors are installed at fixed locations and to communicate with monitoring systems.

SUMMARY

A detachable filter assembly includes a filter, a filter assembly housing defining a body of the filter assembly, an attachment mechanism configured to couple to a sensor installation, a securing mechanism configured to mate with a mating feature on the sensor installation, and a calibration port configured to provide a direct fluid pathway to the sensor installation.

DETAILED DESCRIPTION

Figure 1:
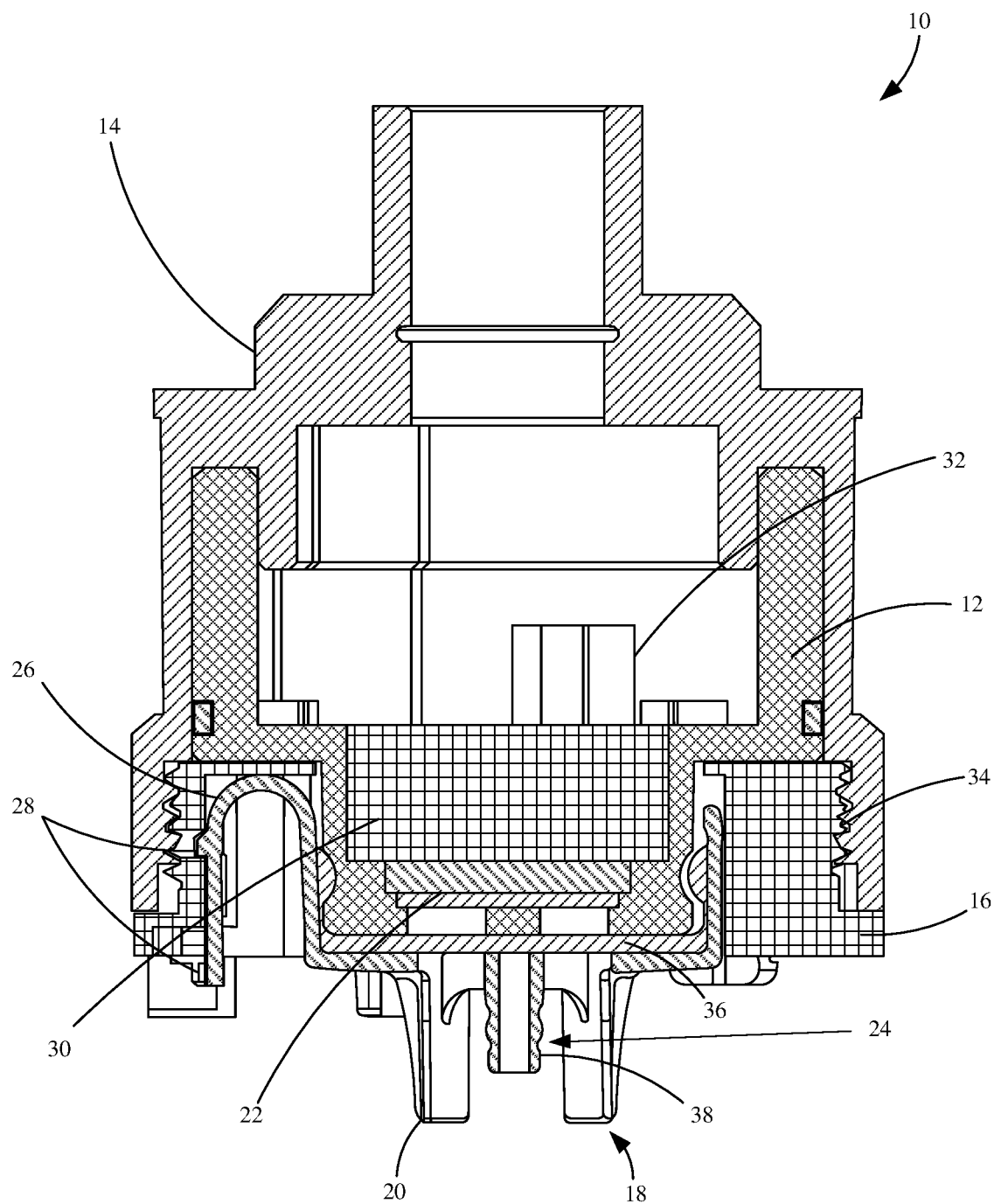
FIG. 1 is a partial cutaway view showing one example of a sensor module installation.

Gas detectors are often deployed in industrial environments. These gas detectors may be configured to detect the presence of various gases including combustible, toxic, flammable gases, and/or oxygen depletion in the environment. These gas detectors are often placed in a fixed location that can be difficult to access. Sometimes the environments in those locations can be hazardous. For example, they may contain combustible, toxic, or flammable gases and liquids.

The sensors typically employed within gas detectors need to be calibrated with target gas and clean air during installation. These sensors will often deteriorate and lose calibration over the sensor's service life or they can become contaminated after an extended period of operating in an environment that is polluted from contaminants such as dust or debris. This will dull the sensitivity of the sensor and its ability to pick up smaller traces of gases.

Calibration is needed to ensure that the analog, digital, and discrete outputs of the sensor are all accurately transmitting the target gas concentration detected by the sensor. Calibration correctly zeroes the sensor to ideal air conditions. Once zeroed, the target gas must be connected to the sensor to induce a point of reference for detection. However, these sensors are often located in inconvenient locations within industrial environments thereby making it difficult to calibrate or otherwise maintain the sensor. These locations can be difficult to reach or access and may contain dangerous densities of combustible, toxic or flammable gases, or may otherwise be deplete of oxygen. Therefore, calibration with current systems can be time consuming and expose workers to dangerous conditions.

Filters are typically employed within the gas detectors. These filters are meant to protect the sensors from contamination from dust or debris while still allowing the sensor to access target gases. This is meant to reduce the needed maintenance on the sensor during its service lifetime. However, these filters can become clogged or otherwise deteriorate over time which reduces the sensor's accessibility to target gases and need to be maintained or replaced. As well as being located in inconvenient or hazardous locations, current systems often require a lengthy disassembly of a gas detector installation in order to replace or maintain these filters. This increases the cost of service as well as a worker's exposure to hazardous conditions.

A gas detector system that will reduce the burden, danger and expense associated with sensor maintenance while still allowing for accurate measurements is needed. One such system, provided herein, includes a self-contained calibration apparatus. The calibration apparatus comprises a filter assembly that includes a housing, a calibration port and attachment and securing mechanisms as a separate and removable assembly from a sensor installation. This design allows for quicker and easier replacement and maintenance of the sensor and filter within the gas detector. The calibration port allows for fixed gas calibration to be performed by a user on various installations thereby reducing the cost and burden of calibration in hazardous and inconvenient locations.

FIG. 1 is a partial cutaway view showing one example of a sensor module installation. Sensor module installation 10 includes sensor module 12, sensor module housing 14, sensor module housing cover 16, filter assembly 18, filter assembly housing 20, filter 22, calibration port 24, attachment mechanisms 26, securing mechanisms 28, sensing element 30, electronics 32, threads 34, gasket 36, and coupling mechanisms 38.

Sensor module 12 contains sensing element 30 and electronics 32. Sensing element 30 can be any number of process analytics sensors used in process environments but is illustratively shown as a gas sensor. Sensing element 30 is electrically coupled to electronics 32. Electronics 32 can contain any number of components, including, but not limited to, processors, measurement circuitry, communication circuitry, and/or controllers. For example, in one embodiment, electronics 32 could include measurement circuitry configured to receive a signal from sensing element 30, a processor configured to calculate a sensor-related output, communication logic configured to generate a signal indicative of the sensor-related output, and communicate wirelessly via a transmitter, or through a wired loop, to a display panel or a user interface (such as a computer in a control room). Electronics 32 could include a controller configured to generate a control signal to have sensor installation 10 preform a function based on the sensor-related output or have some other aspect of a process control system perform a function based on the sensor-related output, like the output of an alarm or notification, or the adjustment of a valve, for example.

Sensor module 12 is contained within sensor module housing 14 and sensor module housing cover 16. Cover 16 is placed over module 12 and couples to housing 14 by threads 34. Threads 34 are on a surface of housing 14 and a surface of cover 16. While threads are illustratively shown, any number of suitable coupling techniques, or combination thereof, could be used, including, but not limited to, press fit, keying features, latches, barbs, other mating features, etc. Housing 14 and cover 16 provide protection to elements within, such as sensing element 30 and electronics 32. Housing 14 and cover 16 could also provide compliance with hazardous locations standards by forming flame-proof pathways and seals meant to prevent the flow and escape of fluids from the sensor module installation. Sensor module installation 10 could be made from any number of suitable materials, but particularly those suited for compliance with hazardous location standards. Particularly, but not limited to, non-ferrous metals containing high thermal conductivity like copper-aluminum alloys, stainless steel, silver, aluminum and galvanized steel, for example, or non-metallic, non-sparking materials like plastics, woods, and thermoplastic polymers. Such materials are known and commonly used in the manufacture of gas sensor installation and non-sparking and explosion-proof equipment.

Filter assembly 18 is a field-replaceable, separable and removable component of installation 10. Filter assembly 18 preferably includes a filter assembly housing 20, filter 22 and gasket 36. Filter assembly housing 20, which includes attachment mechanisms 26 and securing mechanisms 28, is configured to prevent contaminants such as debris and dust from reaching filter 22 and sensing element 30. Filter 22 and gasket 36 are configured to prevent contaminants such as debris and dust from reaching sensing element 30 and an interior of sensor installation 10. In one embodiment, filter 22 and gasket 36 are configured to provide compliance with safety-related standards (e.g. Ingress Protection Rating 66 "IP66" or Ingress Protection Rating 67 "IP67"). In another embodiment, filter 22 and gasket 36 are configured to provide compliance with safety-related standards (e.g. National Electrical Manufactures Association Standards "NEMA").

Attachment mechanisms 26 and securing mechanisms 28 allow for a tool-less coupling of filter assembly 18 to installation 10. While embodiments are generally described where the attachment mechanism and securing mechanism are separate, it is expressly contemplated that embodiments can be practiced where a single integrated member accomplishes both functions. For example, upon applying an insertion force, attachment mechanisms 26 and securing mechanisms 28 may couple to a receiving portion of installation 10, thereby securing filter assembly 18 to installation 10 without requiring any tools. Filter assembly 18 may then be removed by hand from installation 10 by compressing attachment mechanisms 26 and securing mechanisms 28 and pulling filter assembly 18 away from installation 10. Attachment mechanisms 26 are shown as an inverted "U" shaped body but could be any suitable shape to allow for tool-less coupling and removal. Securing mechanisms 28 are shown as latching features with a mating/receiving pair in installation 10 but could be any suitable feature for securing filter assembly 18 to installation 10 such as, but not limited to, inserts, barbs, etc. Filter assembly 18 could also include an alignment feature such that alignment mechanisms 26 and securing mechanisms 28 have a single proper orientation (a single rotatable orientation). This alignment feature could be, but is not limited to, a keying feature on a surface of filter assembly 18 with a mating feature on a surface of installation 10.

In one embodiment, upon coupling filter assembly 18 to installation 10, filter 22 and gasket 36 become compressed, creating a seal between filter assembly 18 and installation 10. In one embodiment, this compression provides a safety-rated seal (e.g. IP66, IP67 or NEMA) while still allowing sensing element 30 to be responsive in accordance with known industry standards. Filter 22 may comprise a permeable material configured to allow for passage of certain fluids while protecting sensing element 30. Filter 22 may also comprise a hydrophobic, permeable material designed to protect sensing element 30 from splashing and spraying liquids and from dust and other debris that may inhibit performance of sensing element 30. Filter 22 is, in one embodiment, configured to protect sensing element 30 from moisture and contaminants such as debris and dust in accordance with an Ingress Protection (IP) standard. In another embodiment, Filter 22 is configured to protect sensing element 20 from moisture and contaminants such as debris and dust in accordance with NEMA standards. As mentioned above, filter 22 may become clogged or otherwise degraded and require maintenance or replacement. Filter assembly 18 allows for less burdensome installation, maintenance and replacement of filter 22 by, for example, tool-less coupling and removal of filter assembly 18.

Filter assembly also includes calibration port 24 and coupling mechanisms 38. Calibration port 24 is built-in to filter assembly 18 and provides a fluid flow passageway with direct flow access to sensing element 30. Calibration port 24 allows a calibration hose to be permanently installed on installation 10. The calibration hose is secured on calibration port 24 by coupling mechanisms 38. Coupling mechanisms 38 are illustratively shown as barbs, but could also comprise other suitable techniques for securing the calibration hose to calibration port 24, including latches, hooks, mating pairs such as keying features, threads, inserts, etc.

Figure 2:
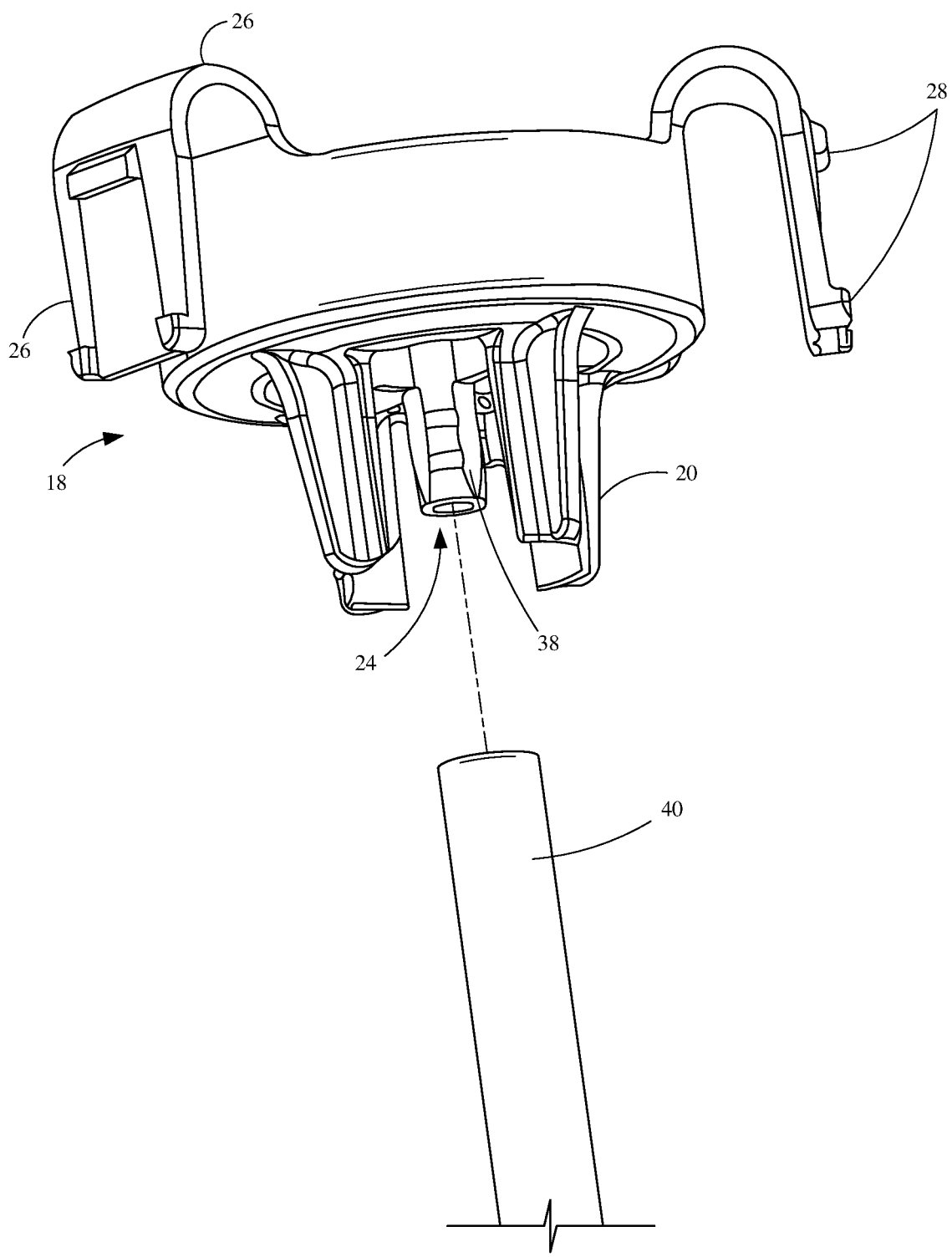
FIG. 2 is a perspective view showing one example of a filter assembly.

FIG. 2 is a perspective view showing one example of a filter assembly. Filter assembly 18 includes filter assembly housing 20, calibration port 24, attachment mechanisms 26, securing mechanisms 28, coupling mechanisms 38 and calibration hose 40. Calibration hose 40 is secured to calibration port 24 by coupling mechanisms 38. This allows calibration fluids to flow directly from calibration hose 40 into calibration port 24 through a fluid flow passageway with direct flow access to sensor element 30. Filter assembly 18 allows for a fixed and permanent installation of a calibration fluid mechanism (e.g. calibration hose 40) such that calibration can be done with less burden, danger, and expense, particularly when a sensor installation (e.g. installation 10) is in a difficult to access or hazardous location by utilizing calibration hose 40 to feed calibration fluid to sensing element 30. Calibration hose 40 can be of any length desired to allow a user to calibrate sensor installation 10 from a safe or easy to access location. Additionally, calibration hose 40, while secured to calibration port 24 by coupling mechanisms 38, can still be removed by a user so that removal of or change of location for installation 10 can be achieved. While calibration hose 40 is illustratively shown as a hose, it could also comprise a pipe, a tube, or any other suitable technique for providing calibration fluids to filter assembly 18. Calibration hose 40 could comprise metal, rubber, polymer, or any other suitable material for transporting calibration fluids.

Figure 3:
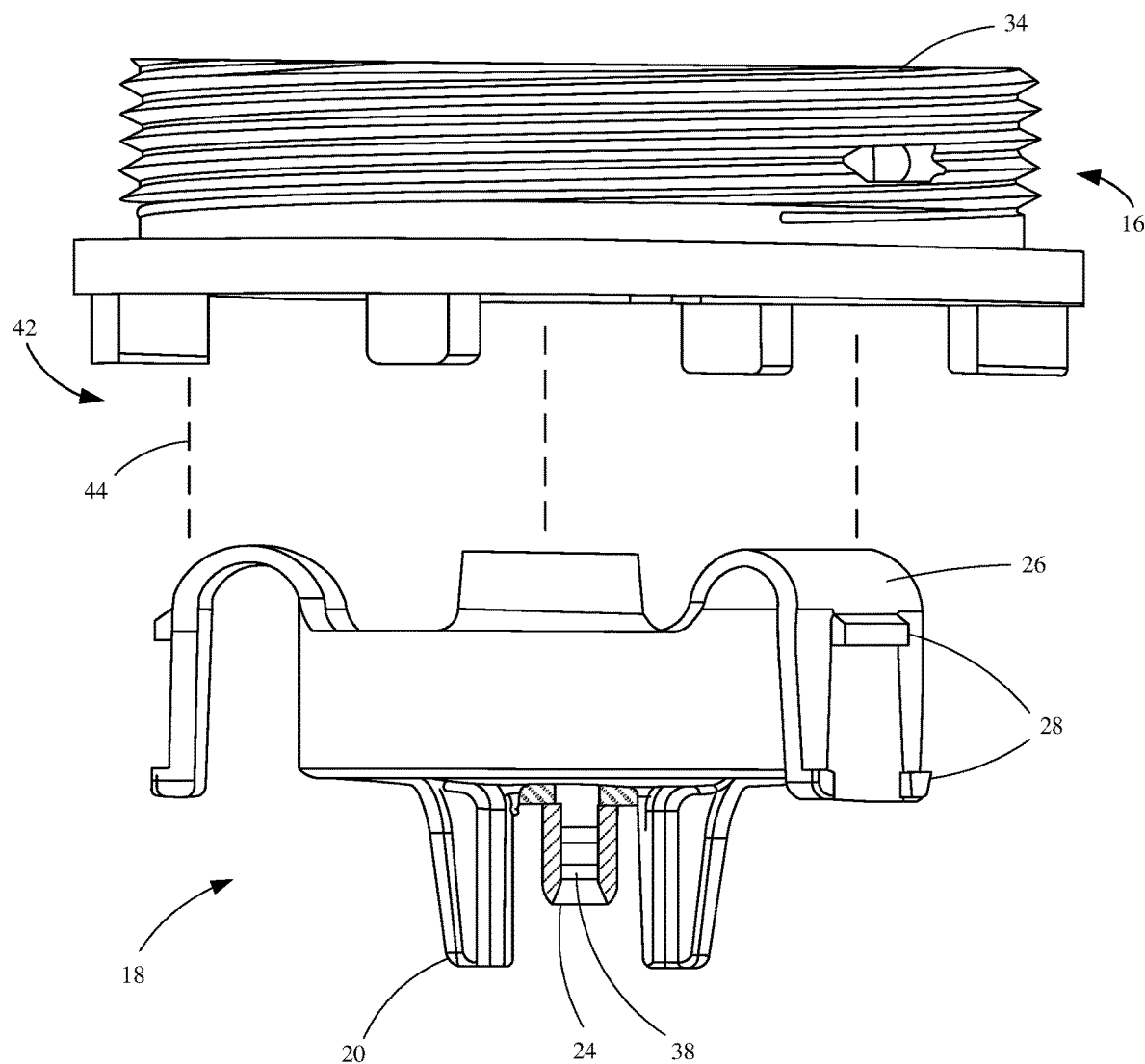
FIG. 3 is a perspective view showing one example of a filter assembly installation.

FIG. 3 is a perspective view showing one example of a filter assembly installation. Filter assembly installation 42 includes sensor module housing cover 16, filter assembly 18, filter assembly housing 20, calibration port 24, attachment mechanisms 26, securing mechanisms 28, threads 34, and coupling mechanisms. Lines 44 are included to indicate a travel direction for filter assembly 18 as it is coupled to sensor module housing cover 16. A user may apply an inserting force, compressing attachment mechanisms 26, while moving filter assembly 18 towards cover 16. As filter assembly 18 is fit into cover 16 a user may receive an audible or otherwise sensory confirmation that securing mechanisms 28 have been properly secured or otherwise received by features within cover 16. To remove filter assembly 18 from cover 16 a user may apply a removal force, compressing attachment mechanisms 26, and pulling filter assembly 18 away from cover 16.

Figure 4:
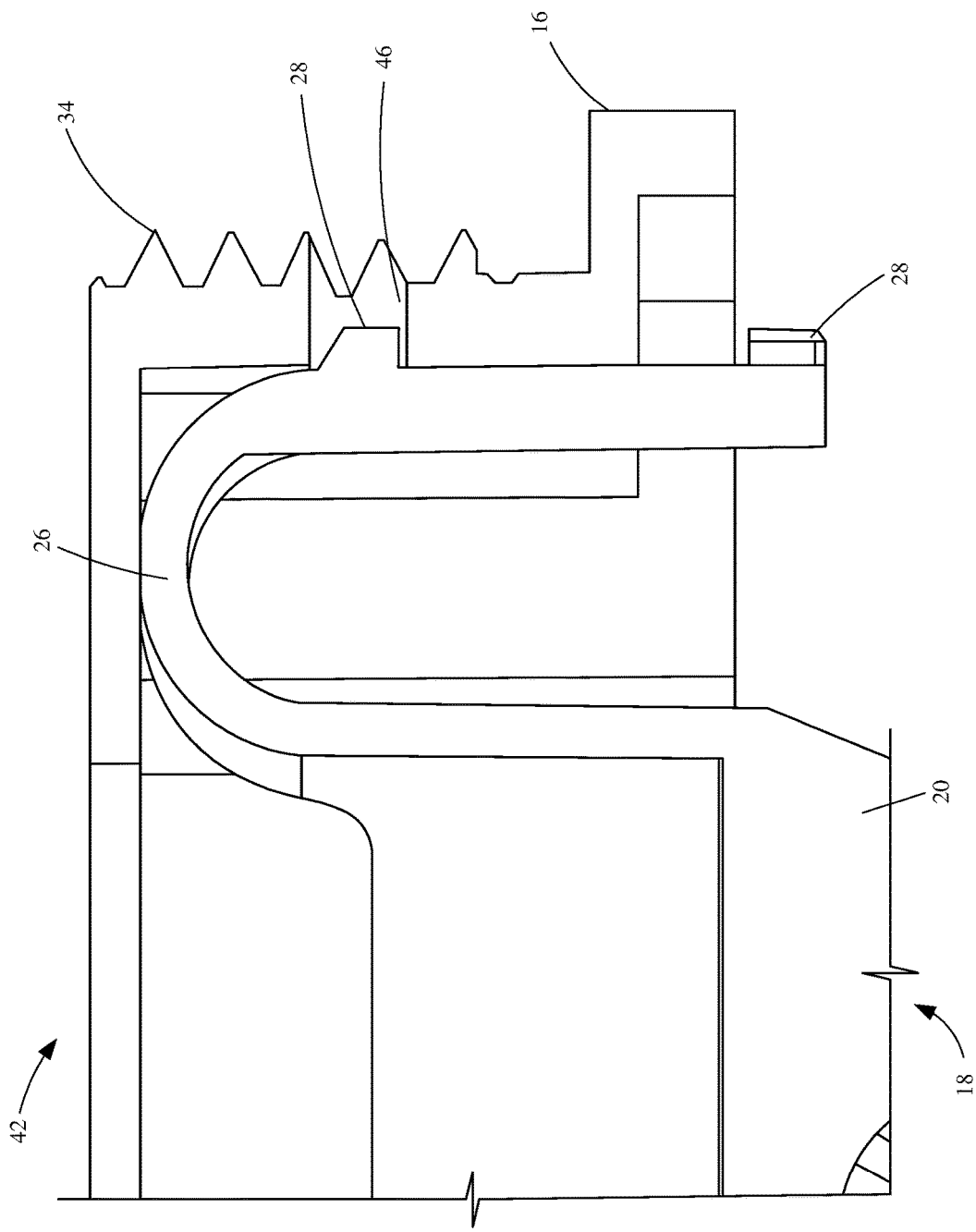
FIG. 4 is a partial cutaway view showing one example of a filter assembly installation.

FIG. 4 is a partial cutaway view showing one example of a filter assembly installation. Filter assembly installation 42 includes sensor module housing cover 16, filter assembly 18, filter assembly housing 20, attachment mechanisms 26, securing mechanisms 28, threads 34 and receiving portion 46. When a user couples filter assembly 18 to cover 16 securing mechanisms 28 are received by receiving portion 46 of cover 16 thereby securing filter assembly 18 to cover 16. This creates a sealed, air tight connection between filter assembly 18 and cover 16. Such a connection allows installation 42 to be in compliance with safety standards for process environments and hazardous locations.

Figure 5:
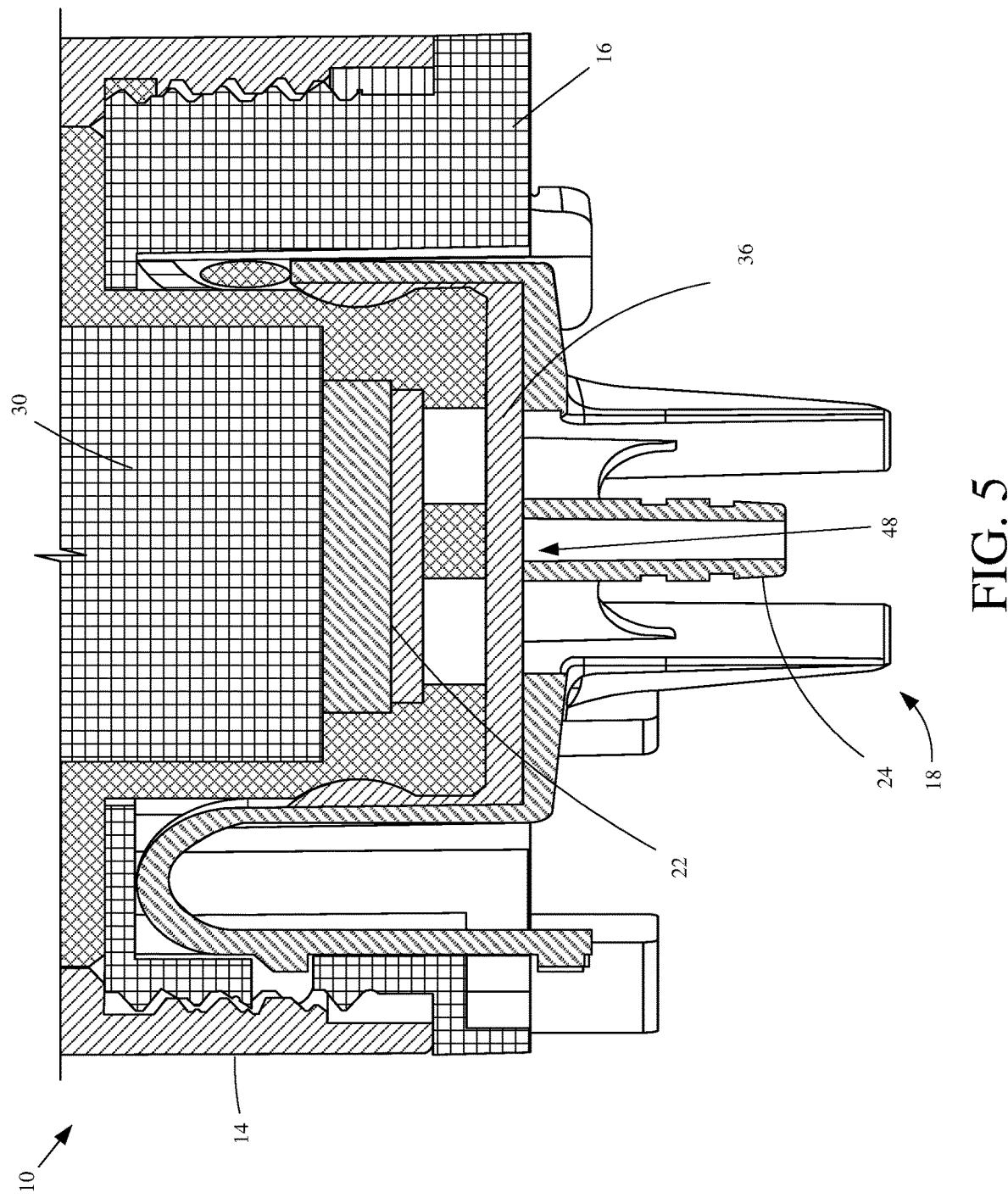
FIG. 5 is a partial cutaway view showing one example of a sensor module installation.

FIG. 5 is a partial cutaway view showing one example of a sensor module installation. Sensor module installation 10 includes sensor module housing 14, sensor module housing cover 16, filter assembly 18, filter 22, calibration port 24, sensing element 30, gasket 36, and calibration fluid flow pathway 48 (indicated by an arrow). When filter assembly 18 is coupled to installation 10 calibration port 24 provides for direct fluid flow via calibration fluid flow pathway 48 to sensing element 30 through filter 22. This is termed "direct fluid flow" even though the fluid flow passes through a filter. Calibration fluid flow comes into installation 10 from an outside source via a connection (e.g. calibration hose 40) where it can be detected by sensing element 30. This fluid flow can be used by sensing element 30 for calibration. Compression of gasket 36 by the coupling of filter assembly 18 and cover 16 ensures a sealable coupling between filter assembly 18 and installation 10.

Figure 6:
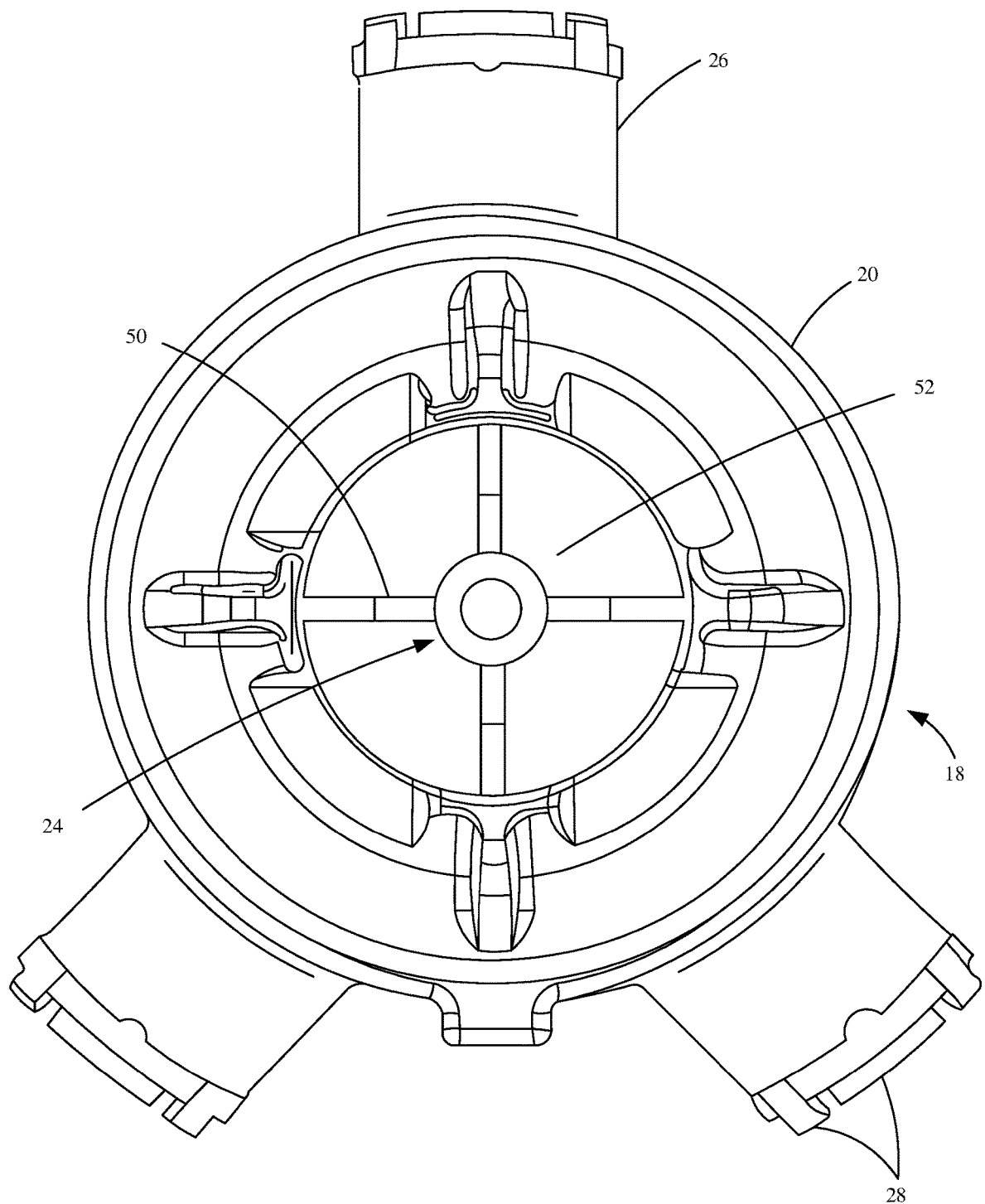
FIG. 6 is a bottom view showing one example of a filter assembly.

FIG. 6 is a bottom view showing one example of a filter assembly. Filter assembly 18 includes filter assembly housing 20, calibration port 24, attachment mechanisms 26, securing mechanisms 28, port attachments 50, and open sensor detection areas 52. As shown, calibration port 24 can be coupled to assembly housing 20 via port attachments 50. Port attachments 50 may be molded as one continuous piece with calibration port 24 and the rest of filter assembly 18, or it may be a separate component otherwise coupled to calibration port 24 and housing 20 by suitable coupling techniques including, but not limited to, soldering, welding, chemical adhesion, chemical bonding, etc. As can be seen, filter assembly 18 allows for a permanent and fixed calibration port (e.g. port 40) while taking very little surface away from a sensor (e.g. sensing element 30). Port attachments 50 allow for secure coupling of calibration port 24 to housing 20 while still allowing open sensor detection areas 52 such that a sensor (e.g. sensing element 30) can still access process fluid for detecting process flow characteristics. This shows how a calibration hose (e.g. calibration hose 40) can be permanently secured for calibration while still allowing for the desired sensing. In one embodiment, a calibration hose is permanently secured to the filter assembly during the life of the sensor installation without affecting the operability of the sensing element which can access process fluids via the open sensor detection areas.

Figure 7:
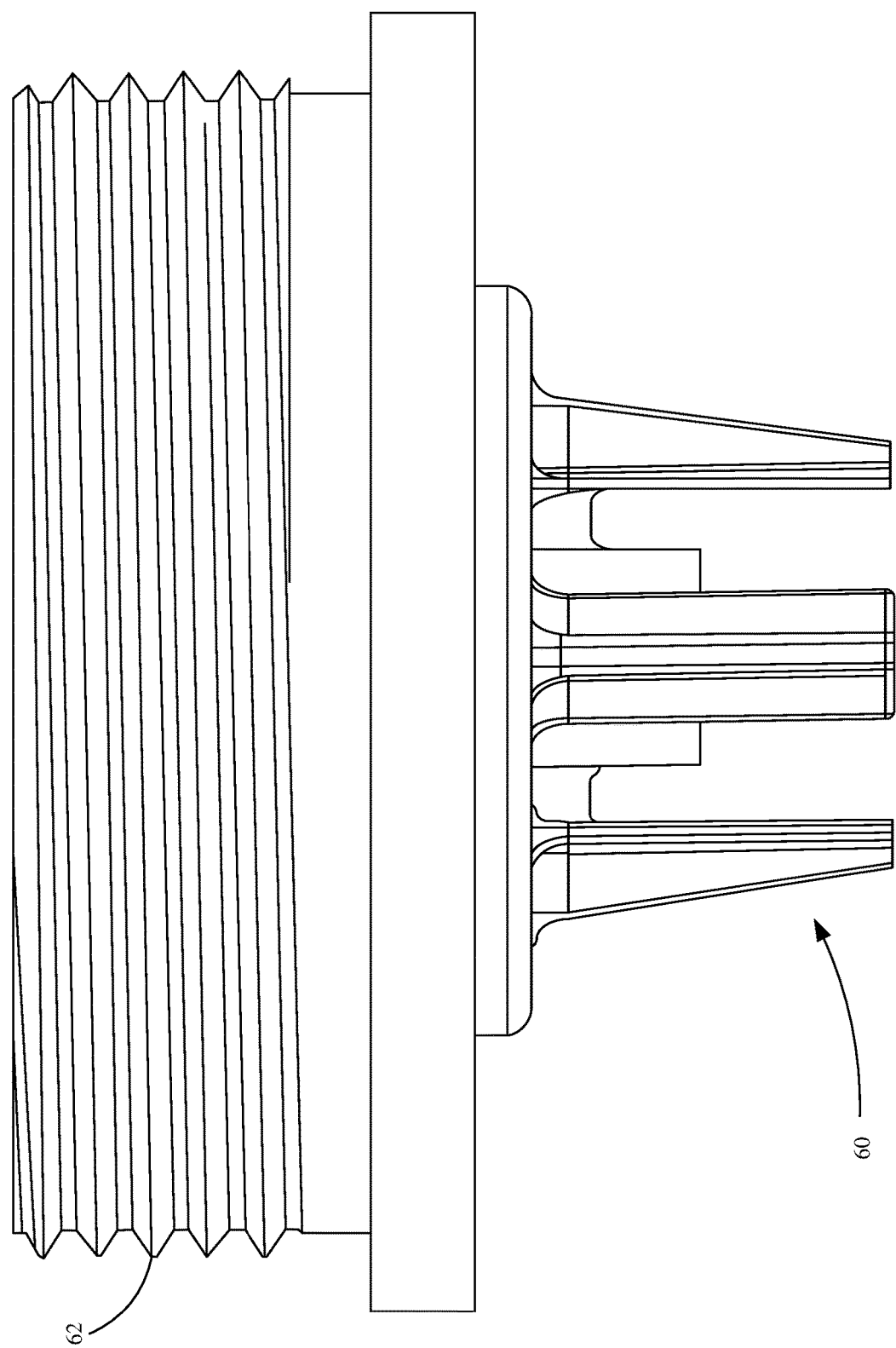
FIG. 7 is a perspective view showing one example of a filter assembly.

FIG. 7 is a perspective view showing one example of a filter assembly. Filter assembly 60 includes threads 62. Filter assembly 60 is similar to filter assembly 18 except that assembly 60 is threadably coupled to a sensor module installation (e.g. installation 10). Filter assembly 60 is coupled to a sensor module installation (e.g. installation 10) via threads 62. This embodiment still allows for removal of a filter assembly for maintenance and replacement of a filter while increasing the resistance of the coupling between a filter assembly and a sensor module installation to outside forces such as vibrations.

Figure 8:
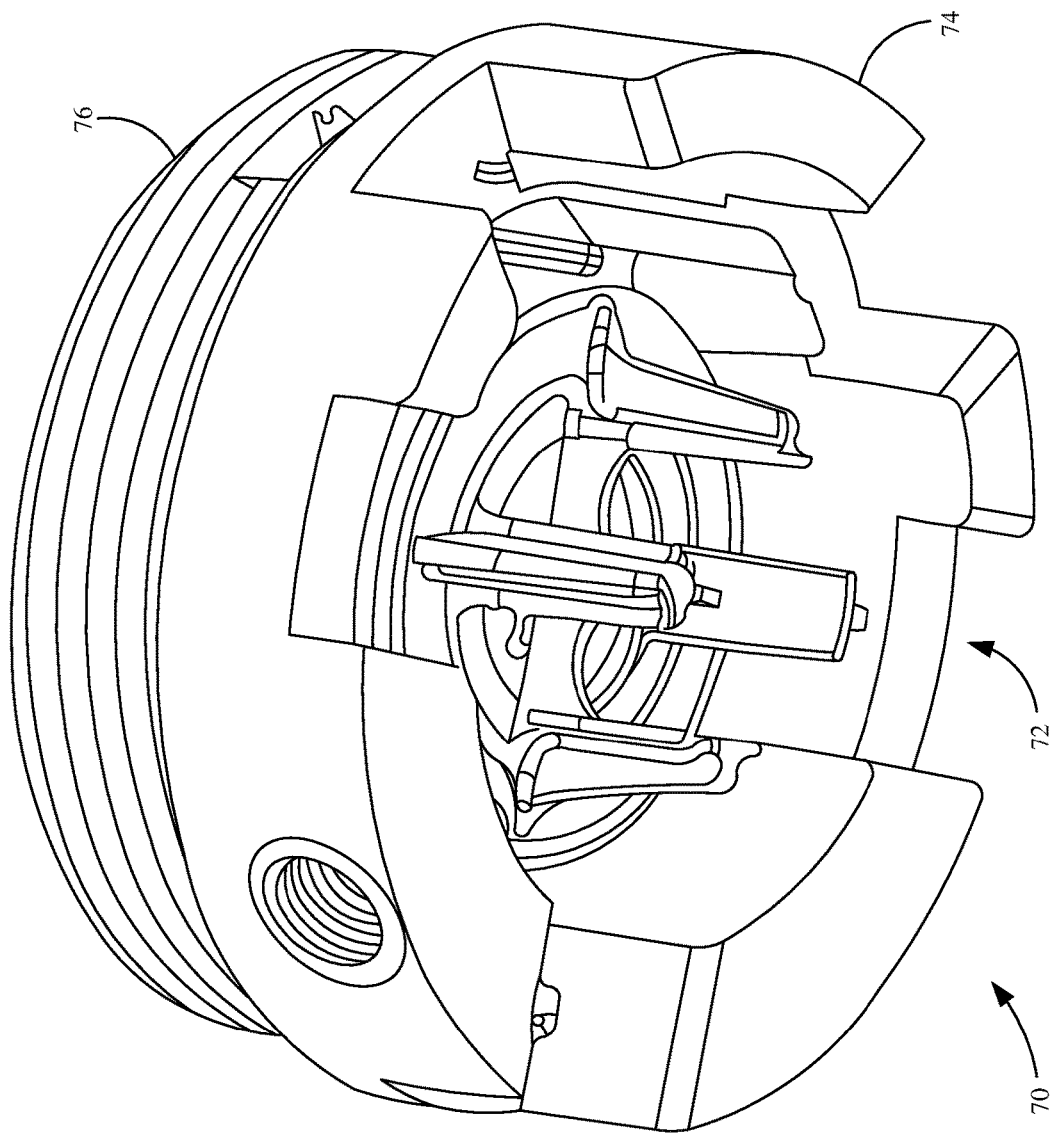
FIG. 8 is a perspective view showing one example of a filter assembly installation.

FIG. 8 is a perspective view showing one example of a filter assembly installation. Filter assembly installation 70 includes filter assembly 72, attachment mechanism 74, and threads 76. Filter assembly 72 is removably coupled to attachment mechanism 74. Attachment mechanism includes threads 76 to secure attachment mechanism 74 to a sensor module housing installation (e.g. installation 10). This embodiment still allows for removal of a filter assembly for maintenance and replacement of a filter while increasing the resistance of the coupling between a filter assembly and a sensor module installation to outside forces such as vibrations.

Figure 9:
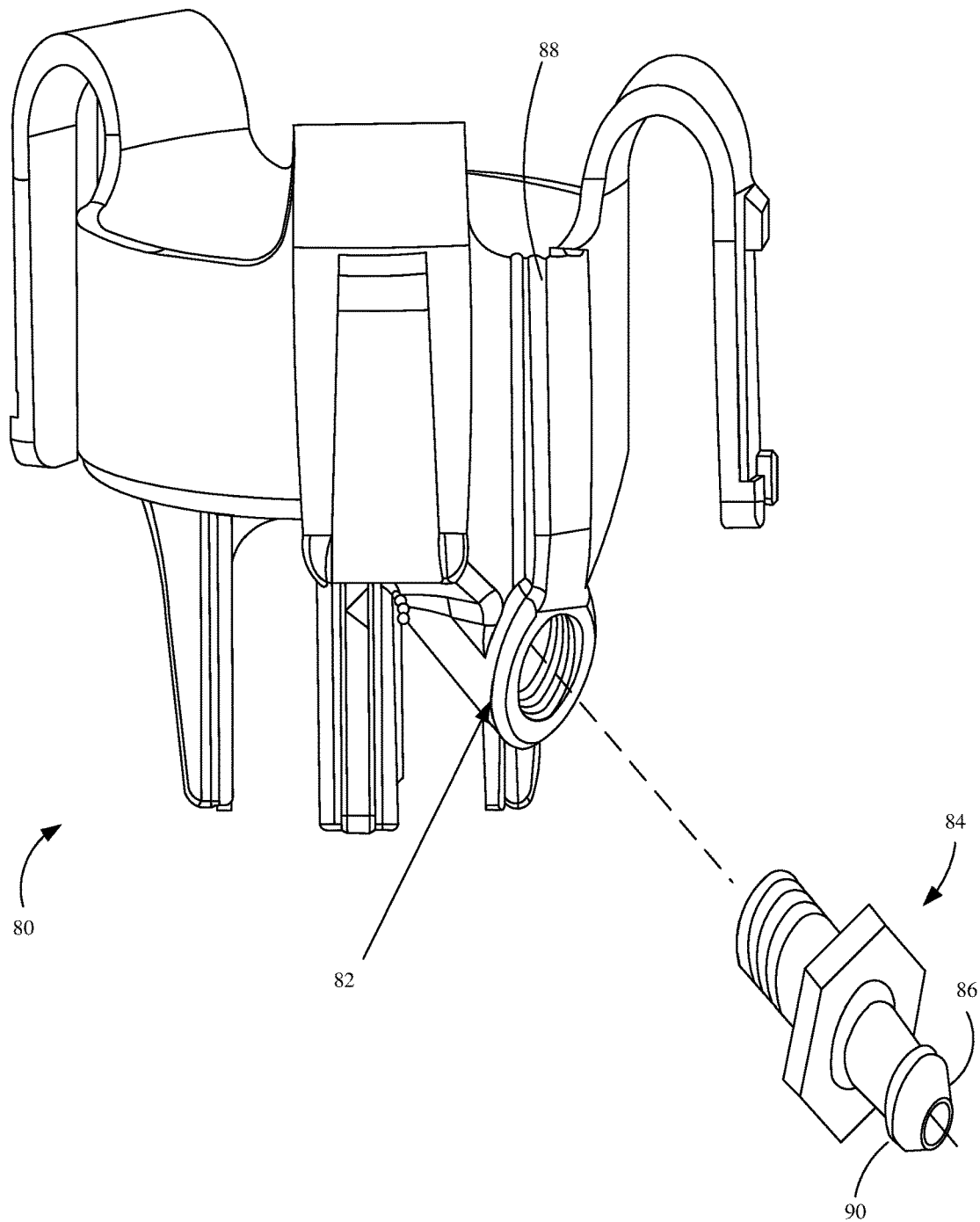
FIG. 9 is a perspective view showing one example of a filter assembly.

FIG. 9 is a perspective view showing one example of a filter assembly. Filter assembly 80 includes attachment hole 82, calibration fitting 84, calibration port 86, alignment feature 88 and coupling mechanism 90. Filter assembly 80 is similar to filter assembly 18 except for the placement and coupling of calibration port 86. Filter assembly 80, instead, provides the calibration fluid flow coming from an offset angle. Calibration fitting 84 includes calibration port 86 and coupling mechanism 90. Calibration fitting could comprise, for example, Swagelok or other suitable pipe or tube fittings. Calibration fitting 84 is coupled to attachment hole 82. While threads are illustratively shown, calibration fitting 84 could be coupled to attachment hole 82 by any suitable techniques including, but not limited to, press fitting, or mating features like a keying feature or other protrusions on an exterior surface of calibration fitting 84 and a receiving feature on an interior surface of attachment hole 82. This design allows for a removable filter assembly while increasing the size of open sensor detection areas. Coupling mechanism 90 is similar to coupling mechanism 38 and allows for a calibration hose (e.g. calibration hose 40) to be permanently fixed to filter assembly 80. Alignment feature 88 provides for one single proper orientation (a single rotatable orientation). Alignment feature may slidably couple to a sensor module housing installation (e.g. installation 10) via a mating feature on an interior surface of the installation. While alignment feature 88 is illustratively shown as a keying feature, other suitable techniques could be used such as, but not limited to, latches, barbs, other protrusions with receiving ends on an interior surface of a sensor module installation, etc. This design allows for less burdensome coupling of filter assembly 80 to a sensor module installation.

Figure 10:
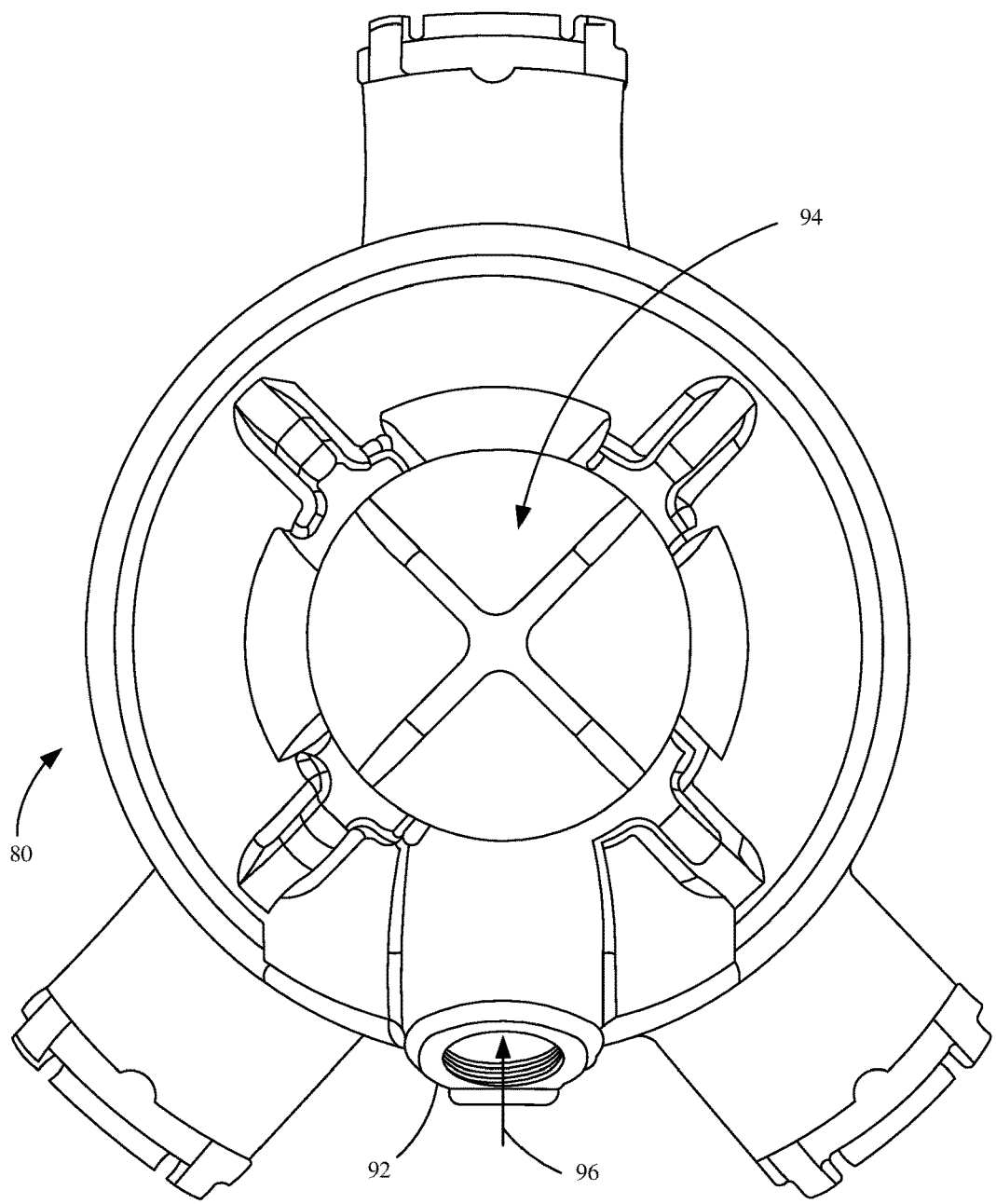
FIG. 10 is a bottom view showing one example of a filter assembly.

FIG. 10 is a bottom view showing one example of a filter assembly. Filter assembly 80 includes attachment hole 92, open sensor detection areas 94, and calibration fluid flow pathway 96 (indicated by an arrow). This design allows a direct calibration fluid flow pathway 96 to a sensor (e.g. sensing element 30) while increasing the size of open sensor detection areas 94.

Figure 11:
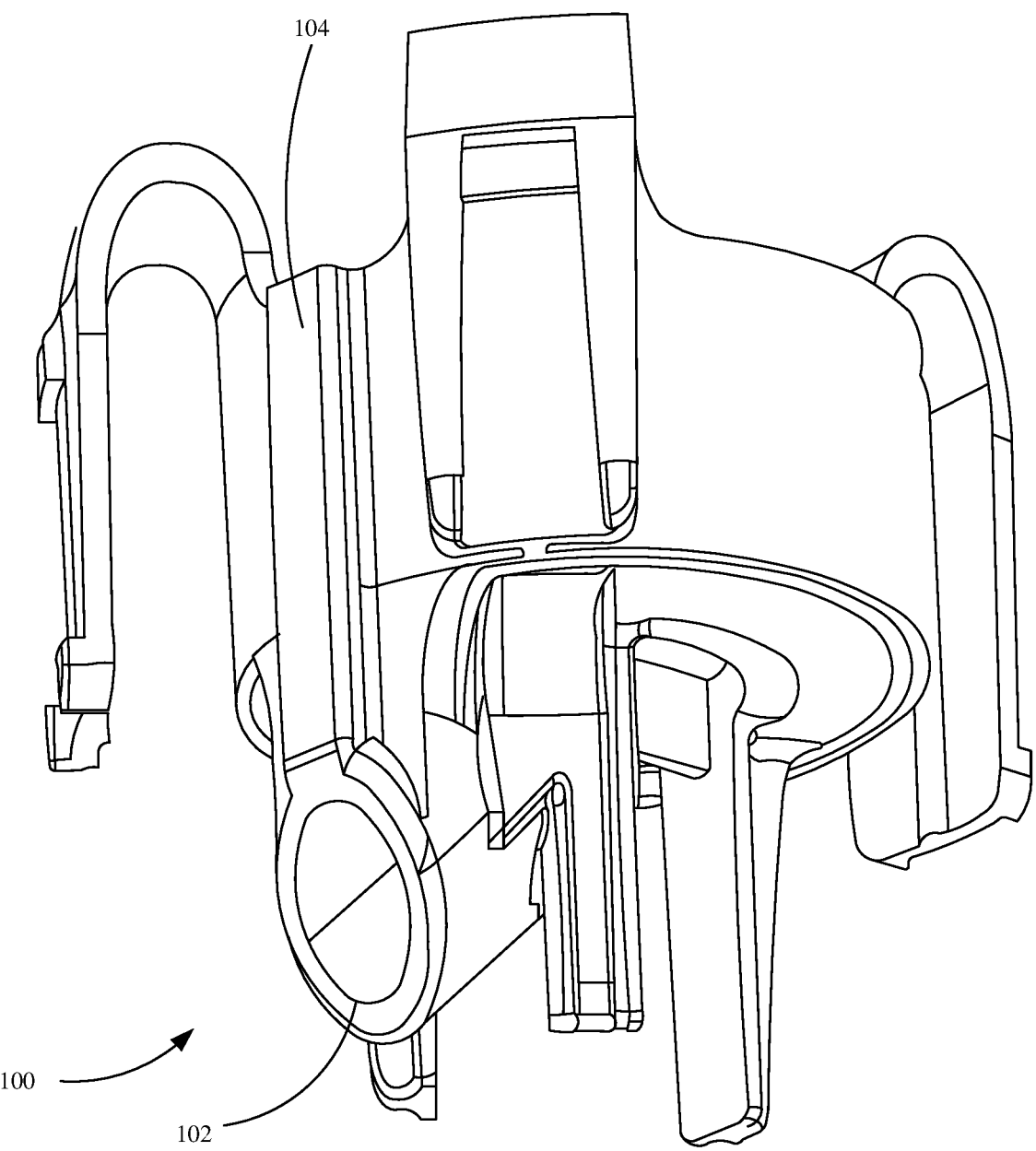
FIG. 11 is a perspective view showing one example of a filter assembly.

FIG. 11 is a perspective view showing one example of a filter assembly. Filter assembly 100 includes attachment hole 102 and alignment feature 104. Filter assembly 100 is similar to filter assembly 80 except that filter assembly includes an enclosed calibration fluid flow pathway (shown below).

Figure 12:
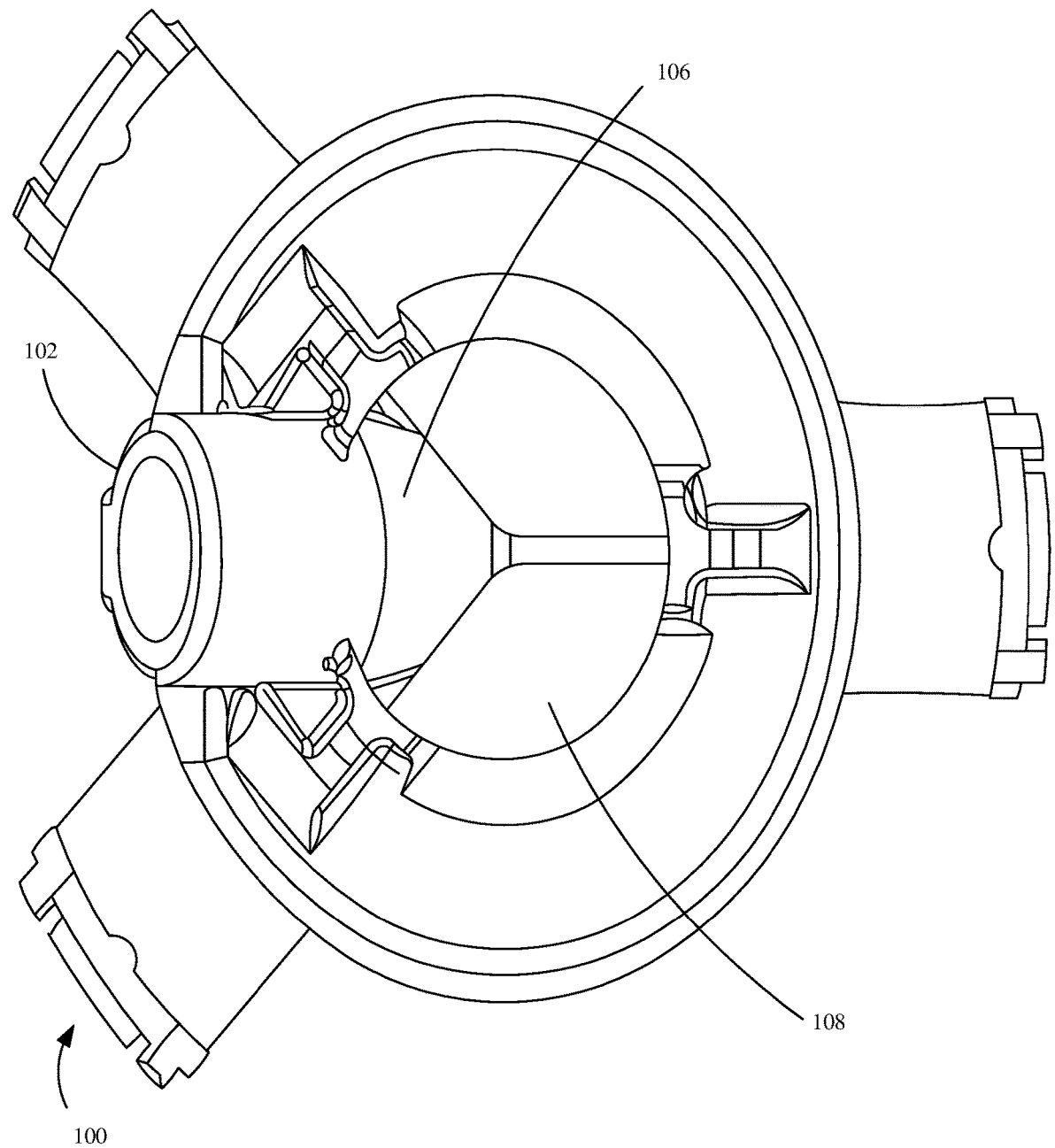
FIG. 12 is a bottom view showing one example of a filter assembly.

FIG. 12 is a bottom view showing one example of a filter assembly. Filter assembly 100 includes attachment hole 102, enclosed calibration fluid flow pathway 106, and open sensor detection areas 108. Enclosed pathway 106 allows for flow of calibration fluids towards a sensor (e.g. sensing element 30) for calibration while protecting the flow of calibration fluids from outside forces, including, but not limited to, wind gusts, that could interfere with the flow of calibration fluids. This design allows for open sensor detection areas 108 such that a sensor can access process fluids while protecting the flow of calibration fluids from interference.

Figure 13:
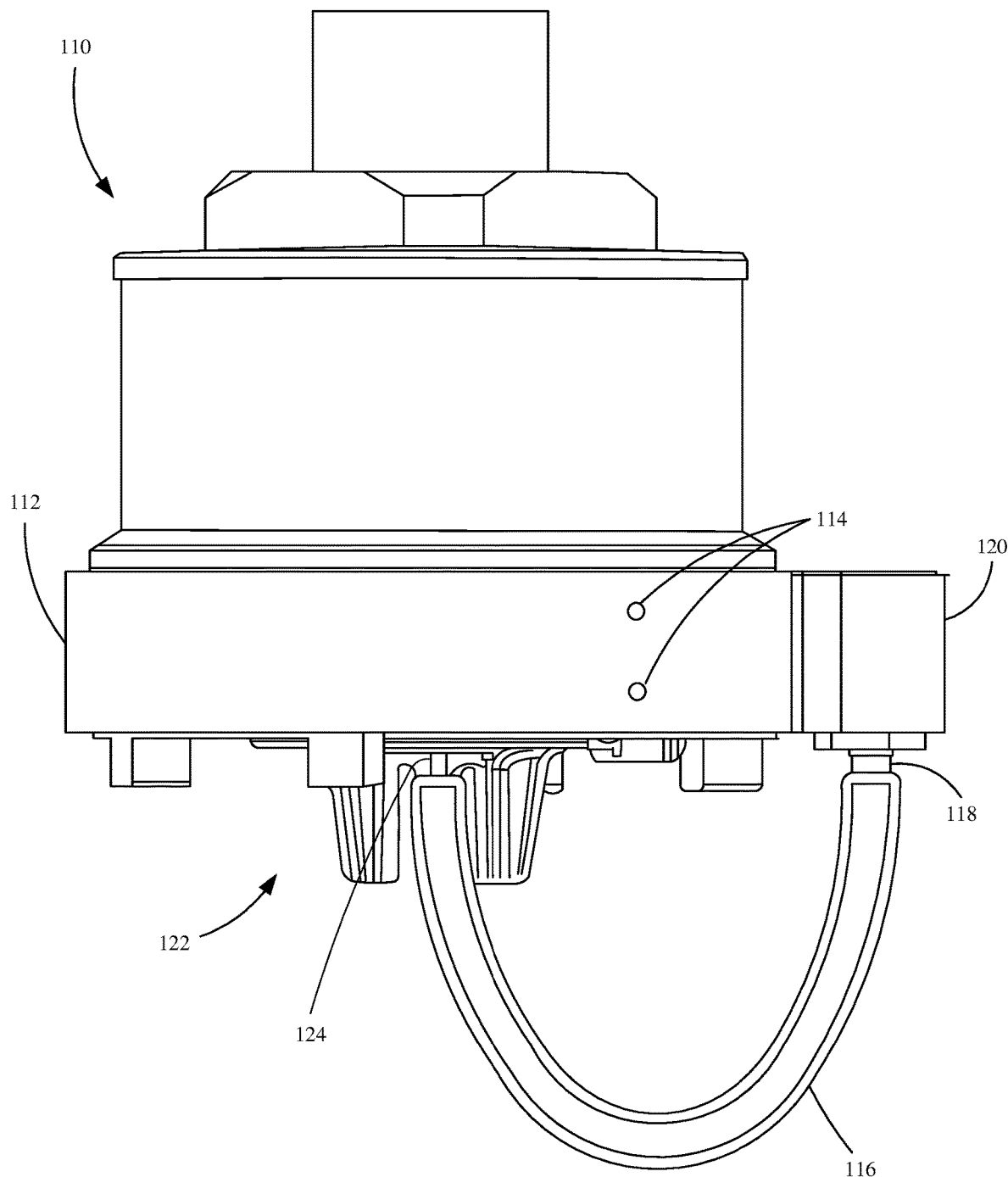
FIG. 13 is a perspective view showing one example of a sensor module installation.

FIG. 13 is a perspective view showing one example of a sensor module installation. Sensor module installation 110 includes locking ring 112, fasteners 114, calibration fluid tube 116, calibration fitting 118, calibration fitting housing 120, filter assembly 122 and calibration port 124. Locking ring 112 fits around an outside perimeter of sensor module installation 110. Ring 112 is secured to installation 110 by fasteners 114 which are spread around the perimeter of ring 112. Fasteners 114 can include any number of suitable fasteners, including, but not limited to, screws, bolts, pins, etc. Ring 112 includes calibration fitting housing 120. Fitting housing 120 secures calibration fitting 118 to ring 112. Fitting 118 can be coupled to housing 120 by any number of suitable techniques, including, but not limited to, threads, press fitting, latches, chemical bonding, welding, soldering, various protrusions with receiving features. Calibration fluid tube 116 is coupled to calibration fitting 118 and calibration port 124. Tube 116 allows for calibration fluid flow from fitting 118 to port 124 whereby a sensor may access a calibration fluid for the purpose of calibration. While tube 116 is illustratively shown as a tube, it could comprise, for example, a hose, pipe, or any other suitable mechanism for transporting calibration fluid. A calibration hose (e.g. hose 40) could be coupled to calibration fitting 118 at an interior of housing 120 thereby allowing calibration of installation 110 from a less burdensome and safer location.

Figure 14:
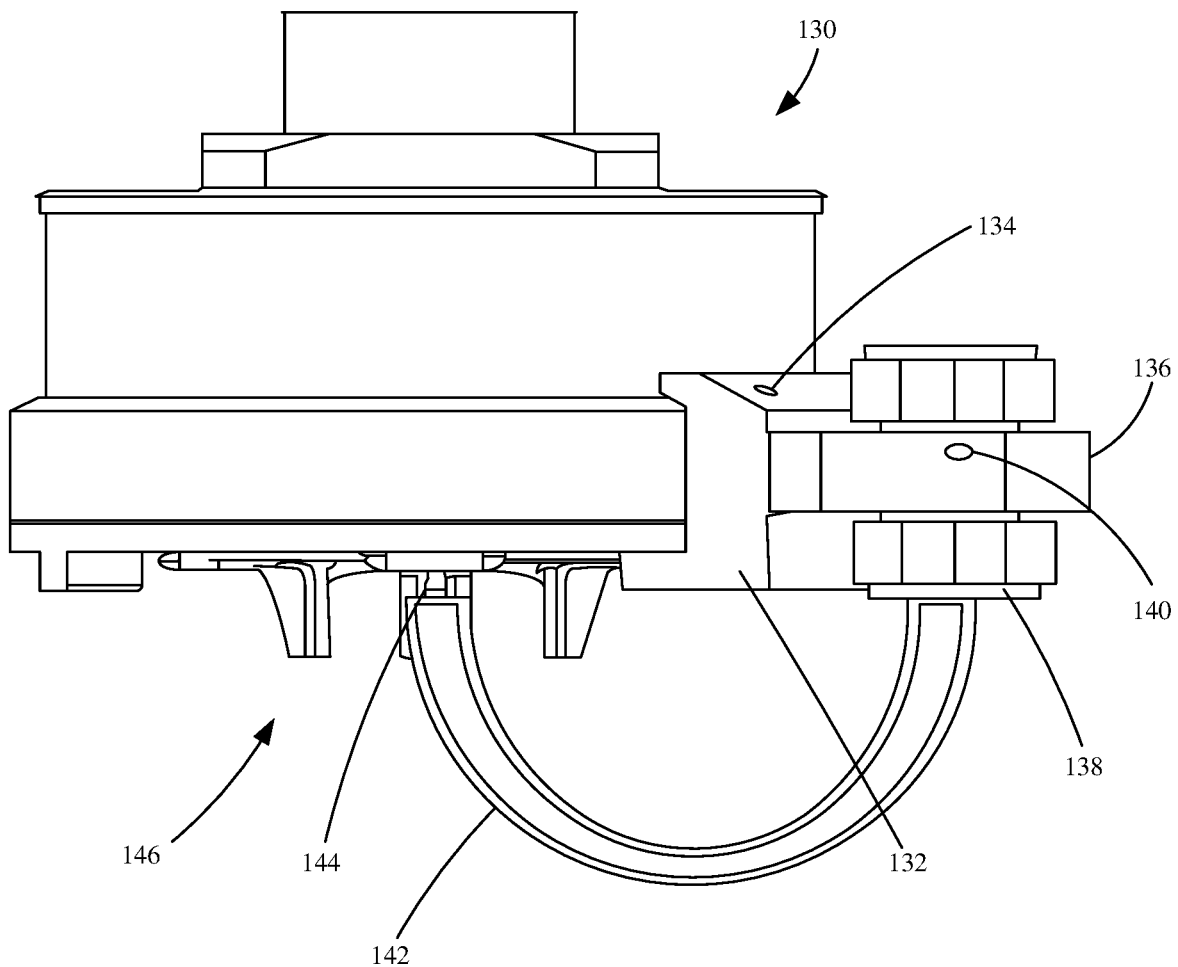
FIG. 14 is a perspective view showing one example of a sensor module installation.

FIG. 14 is a perspective view showing one example of a sensor module installation. Sensor module installation 130 includes clamp 132, fasteners 134, calibration fitting housing 136, calibration fittings 138, fasteners 140, calibration tube 142, calibration port 144 and filter assembly 146. Clamp 132 is slidably fit over an exterior surface of sensor module installation 130. Clamp is secured to installation 110 by fasteners 134 which are placed on an exterior surface of clamp 132. Fasteners 134 can include any number of suitable fasteners, including, but not limited to, screws, bolts, pins, etc. Clamp 132 includes calibration fitting housing 136. Fitting housing 136 secures calibration fitting 138 to clamp 132. Fasteners 140 secure fitting 138 to housing 136. Fasteners 140 can include any number of suitable fasteners, including, but not limited to, screws, bolts, pins, etc. Fitting 138 could be secured to housing 136 by various other techniques, for example, mating pairs of securing mechanisms found on separable ends of fitting 138, such as threads, latches, or other various protrusions with matching receiving features. Calibration fluid tube 142 is coupled to calibration fitting 138 and calibration port 144. Tube 142 allows for calibration fluid flow from fitting 138 to port 144 whereby a sensor may access a calibration fluid for the purpose of calibration. While tube 142 is illustratively shown as a tube, it could comprise, for example, a hose, pipe, or any other suitable mechanism for transporting calibration fluid. A calibration hose (e.g. hose 40) could be coupled to calibration fitting 138 opposite tube 142 thereby allowing calibration of installation 110 from a less burdensome and safer location.

Figure 15:
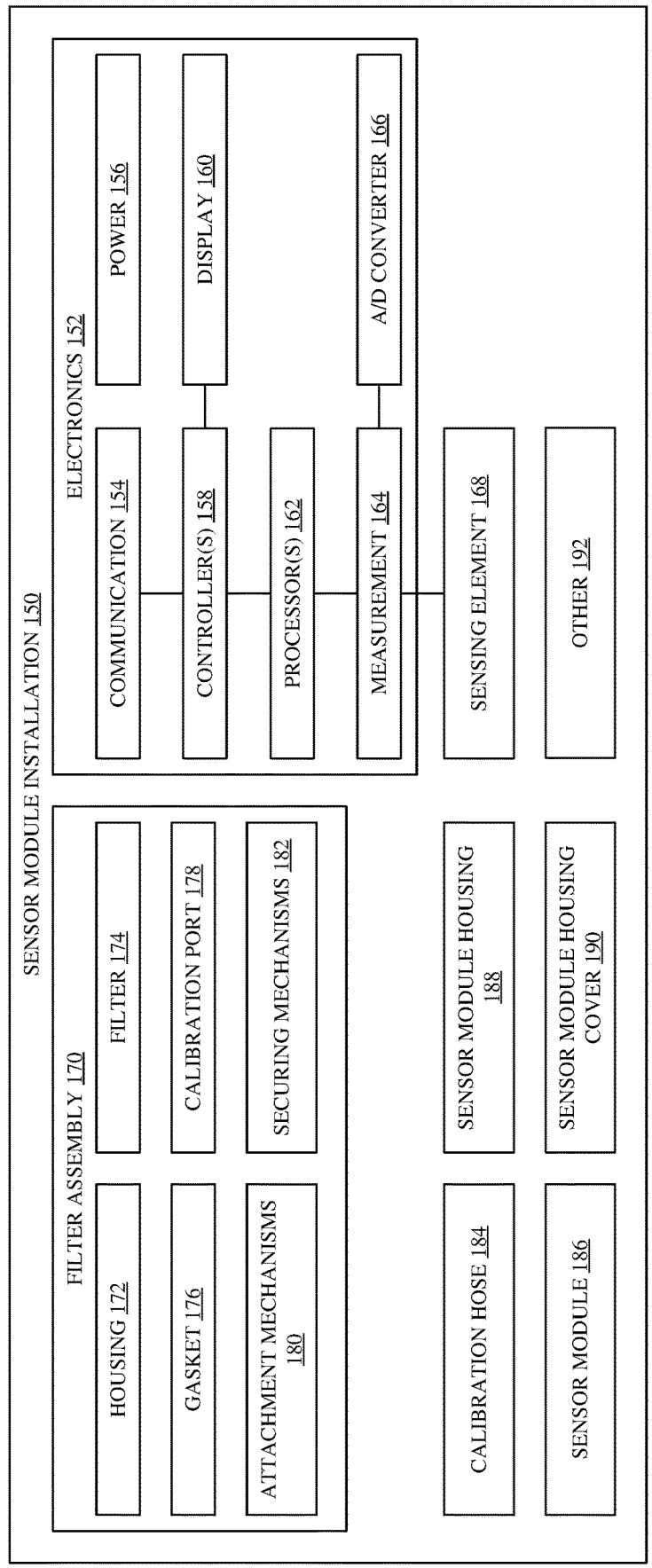
FIG. 15 is a simplified block diagram showing one example of a sensor module installation.

FIG. 15 is a simplified block diagram showing one example of a sensor module installation. Sensor module installation 150 includes electronics 152, communication logic 154, power source 156, controller(s) 158, display 160, processor(s) 162, measurement logic 164, analog/digital convertor 166, sensing element 168, filter assembly 170, filter assembly housing 172, filter 174, gasket 176, calibration port 178, attachment mechanisms 180, securing mechanisms 182, calibration hose 184, sensor module 186, sensor module housing 188, sensor module housing cover 190 and other 192.

Sensing element 168 senses a characteristic of a process flow or environment and generates a sensor signal indicative of the sensed characteristic. Electronics 152 are coupled to sensing element 168. Electronics 152 receive the sensor signal from sensing element 168. Analog/digital convertor 166 converts the sensor signal from analog to digital. Measurement logic 164 receives the converted signal from convertor 166 and generates a measurement signal, indicative of a characteristic of the process flow or environment, based on the sensor signal. For illustrative example, sensor signal from sensing element 168 could be a raw millivolt signal, which would be converted by convertor 166, and then translated into a signal indicative of a concentration of gas by measurement logic 164. Processor(s) 162 receives the measurement signal and generates a sensor-related output based on the measurement signal. For example, processor(s) 162 could receive a concentration of gas measurement and generate a sensor-related output like a derivative of detected gas concentrations. Processor(s) 162 could further compare the sensor-related output to a pre-set threshold for the purposes of calibration, determining accuracy, determining if an adjustment to the input or output of the process flow is needed, and the like.

Controller(s) 158 receive the sensor-related output from processor(s) 162 and issue a control signal based on the sensor-related output. The control signal could be to display the sensed, measured, and determined data on display 160, or some other user interface such as a computer in a control room. The control signal could also generate an alarm or to adjust another element of the process control system through communication logic 154. For example, if a gas concentration measurement came in high or low based on a desired threshold, the controller could reduce or increase the input of a component of the process to adjust the concentration of the detected gas in the process flow or environment by, for example, opening or closing a valve. Similarly, if a determination of the derivative and comparison to a threshold suggested that calibration was necessary, an alarm could be generated by controller 712 which could be sent, via communication logic 154, to a user interface (e.g. display 160) or to an audible or visible alarm feature.

Communication logic 154 receives the control signal from controller(s) 158 and communicates it to a user interface such as a computer in a control room, a remote device, a handheld device, or a display. Communication logic 154 could send the signal via a wired loop or it could communicate wirelessly via a transmitter. Power 156 provides power to the components of electronics 152. Power 156 may be coupled to and draw power from a remote source via power cables coupled to electronics 152, or power 156 could be a self-supplied power source such as, but not limited to, a battery.

Installation 150 includes filter assembly 170. Filter assembly 170 includes filter assembly housing 172, filter 174, gasket 176, calibration port 178, attachment mechanisms 180, and securing mechanisms 182. Filter assembly 170 could be any of the filter assemblies discussed herein (e.g. filter assembly 18). Filter assembly housing 172 defines a body of filter assembly 170 and comprises calibration port 178, attachment mechanisms 180 and securing mechanisms 182. Attachment mechanisms 180 attach filter assembly 170 to installation 150. Securing mechanisms 182 secure filter assembly 170 to installation 150. Calibration port 178 provides a direct flow pathway to sensing element 168 such that sensing element 168 may contact a calibration fluid. Calibration port 178 may include coupling mechanisms (e.g. mechanisms 38) for securing calibration hose 184 to calibration port 178 such that a calibration fluid can be provided to installation 150 from a remote location.

Filter 174 may comprise a permeable material configured to allow for passage of certain fluids while protecting sensing element 156. Filter 174 may also comprise a hydrophobic, permeable material designed to protect sensing element 156 from splashing and spraying liquids and from dust and other debris that may inhibit performance of sensing element 156. Filter 174 is, in one embodiment, configured to protect sensing element 156 from moisture and contaminants such as debris and dust in accordance with an Ingress Protection (IP) standard (e.g. IP66 or IP67). In another embodiment, filter 174 is configured to protect sensing element 156 from moisture and contaminants such as debris and dust in accordance with NEMA standards. Gasket 176 provides a sealable coupling between filter assembly 170 and installation 150 to prevent the flow of certain fluids to electronics 152 which could affect performance of electronics 152. In one embodiment gasket 176 is configured to provide compliance with an Ingress Protection (IP) standard (e.g. IP66 or IP67). In another embodiment, gasket 176 is configured to provide compliance with NEMA standards.

Installation 150 also includes calibration hoses 184, sensor module 186, sensor module housing 188, sensor module housing cover 190, and other 192. Calibration hose 184 may be coupled to filter assembly 170 such that calibration fluids can be supplied to installation 150 from a remote location. Hose 184 could also comprise a pipe, a tube, or any other suitable techniques for supplying a calibration fluid to installation 150. Sensor module 186 may house electronics 152 and sensing element 168 such that these elements of installation 150 may be field-replaceable. Sensor module housing 188 houses sensor module 186 to protect elements of module 186 from damage or contamination. Sensor module housing cover 190 couples to housing 186 (e.g. via threads) to secure module 186 within housing 188 and to further protect module 186 from contamination or damage.

Sensor module housing 188 and cover 190 may, in one embodiment, protect sensor module 186 and the process flow or environment in accordance with flame-proof or other safety standards.

Other 192 is any other feature of installation 150 that may be necessary or advantageous. For example, other 192 could be fasteners, O-rings, like or gaskets. Other 192 could be a transmitter, a display, such as, but not limited to, and LCD display, wiring, and other various electronics. Other 192 could be an audible or visible alarm.

Figure 16:
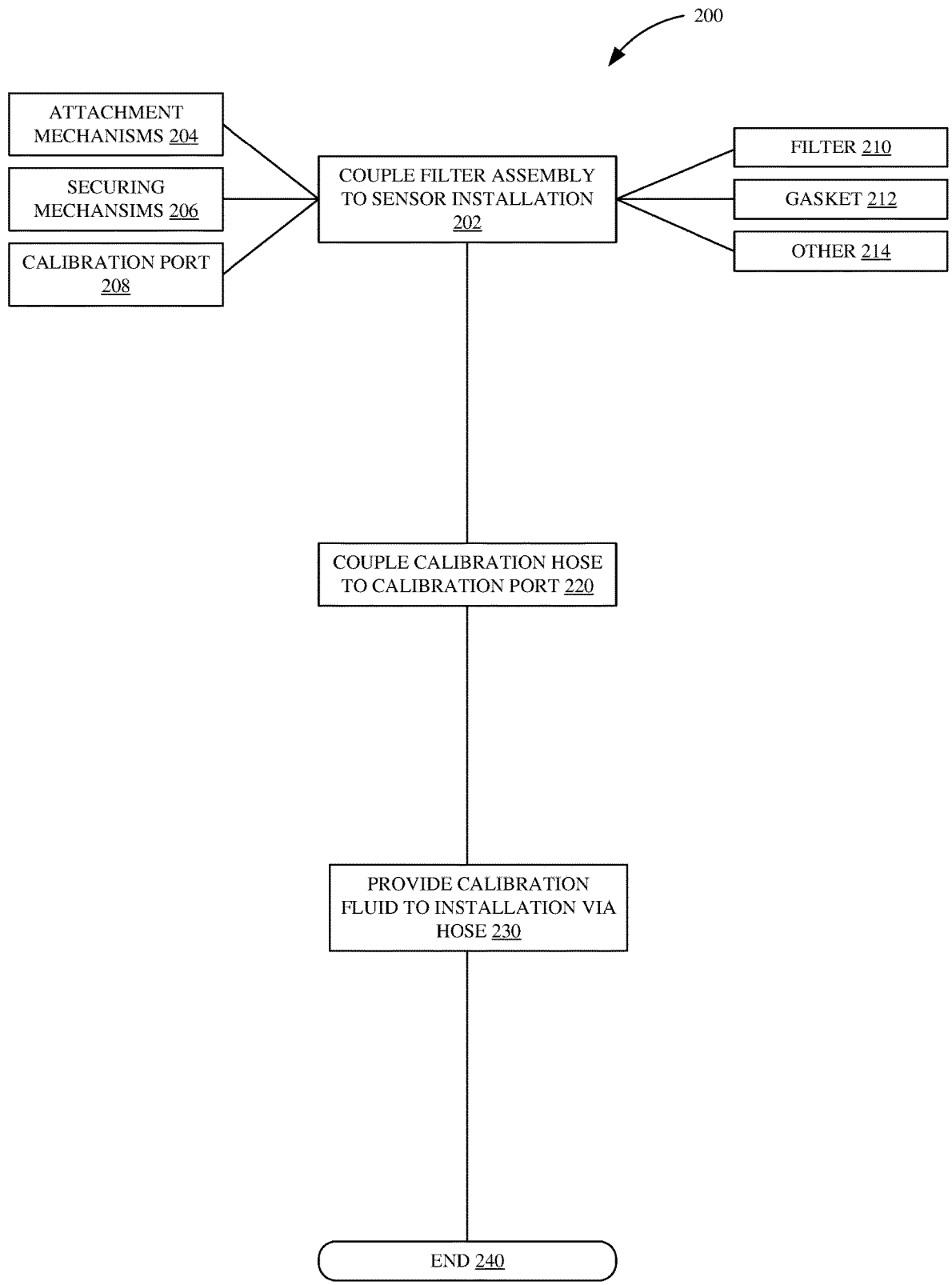
FIG. 16 is a flow diagram showing one example operation of providing calibration fluid to a sensor.

FIG. 16 is a flow diagram showing one example operation of providing calibration fluid to a sensor. Operation 200 starts at block where a filter assembly is coupled to a sensor installation. The filter assembly at block 202 may comprise any of the filter assemblies discussed herein. The filter assembly is coupled to the sensor installation by attachment mechanisms 204 and securing mechanisms 206. Attachment mechanisms 204 may comprise any of the attachment mechanisms discussed herein (e.g. threads or "U Shaped" bodies) or any other suitable technique for securing a filter assembly to a sensor installation. Securing mechanisms 206 may comprise any of the securing mechanisms discussed herein (e.g. mating pairs) or any other suitable techniques for securing a filter assembly to a sensor installation. Filter assembly at block 202 also includes calibration port 208. Calibration port 208 may comprise any of the calibration ports discussed herein (e.g. calibration port 24) or any other suitable calibration port such that a direct flow pathway to a sensing element is created.

The filter assembly at block 202 also includes filter 210. Filter 210 may comprise a permeable material configured to allow for passage of certain fluids (e.g. calibration fluids or target gases) while protecting a sensing element (e.g. element 30). Filter 210 may also comprise a hydrophobic, permeable material designed to protect a sensing element from splashing and spraying liquids and from dust and other debris that may inhibit performance of the sensing element. Filter 210 is, in one embodiment, configured to protect a sensing element from moisture and contaminants such as debris and dust in accordance with an Ingress Protection (IP) standard. The filter assembly also includes gasket 212. Gasket 212 provides a sealable coupling between the filter assembly and the sensor module installation by, for example, compression of gasket 212. The filter assembly may also include other 214. Other 214 could include any feature of a filter assembly that may be necessary or advantageous. For example, other 214 could include o-rings, fasteners, calibration tubes, clamps, fittings, open sensor detection areas, etc.

Operation 200 continues at block 220 where a calibration hose is coupled to the calibration port. The calibration hose at block 220 may comprise any of the calibration hoses discussed herein (e.g. hose 40). The calibration hose can be of any desirable length. The calibration hose may be secured to the calibration port via coupling mechanisms (e.g. mechanisms 38) or by any other suitable techniques for securing a calibration hose to a calibration port. Block 220 could, in some embodiments, further include a calibration fluid tube (e.g. tube 116 or 142) which is coupled to a fitting (e.g. fitting 118 or 138) and to the calibration port. The calibration hose may, in such embodiments, be coupled to an opposite end of the fitting such that the calibration hose and calibration tube are in fluid communication.

Operation 200 continues at block 230 where calibration fluid is provided to a sensor installation via the calibration hose. An operator or automated control system may feed calibration fluid to the sensor installation at a remote location, such as, but not limited to, a location more accessible, less hazardous, or less burdensome to an operator. Calibration fluid may be fed through the calibration hose by, for example, coupling a calibration fluid container to the calibration hose. For illustrative example, an operator may couple a calibration fluid container, such as a gas cylinder containing a calibration gas with known concentrations, to the calibration hose. The calibration fluid may be fed to the sensor installation by the operator turning a valve on the gas cylinder to an open position.

In another embodiment, a calibration fluid container may be permanently installed and coupled to the calibration hose at any desired location. In such an embodiment, an automated control system may feed calibration fluid to the sensor installation by means of, for example, a controller. For illustrative example, an operator in a control room could receive an indication that the sensor installation requires calibration (e.g. an indication from electronics 152). Said operator could then direct (e.g. via a control signal) the automated control system to begin a calibration operation whereby a controller sends a control signal to open, for example, a valve on the calibration fluid container thereby providing calibration fluid to the sensor installation. In another embodiment, the automated control system may not require a control signal from an operator in a control room and may instead automatically begin a calibration operation (thereby providing calibration fluid to the sensor installation) based on the indication that the sensor installation requires calibration. Once calibration fluid is provided to the sensor installation, operation 200 ends at block 240.

Embodiments herein described could be made from any number of suitable materials, including, but not limited to, materials suited for compliance with safety and hazardous location standards. These materials could include, but are not limited to, non-ferrous metals containing high thermal conductivity like copper-aluminum alloys, stainless steel, silver, aluminum and galvanized steel, etc., or non-metallic, non-sparking materials like plastics, polymers, thermoplastic polymers, rubber, or any other suitable materials.

Although the present invention has been described with reference to preferred embodiments, workers skilled in the art will recognize that changes may be made in form and detail without departing from the spirit and scope of the invention. Moreover, while embodiments of the present invention have generally been described with respect to a gas detector, embodiments are practicable with any process analytic sensor.

What is claimed is:
1. A detachable filter assembly comprising:
a filter;
a filter assembly housing defining a body of the filter assembly;
an attachment mechanism configured to couple to a sensor installation;
a securing mechanism configured to mate with a mating feature on the sensor installation;
a calibration port built into the filter assembly, the calibration port having a cylindrical shape and an outer diameter configured to receive a calibration hose and configured to provide a direct fluid pathway to the sensor installation;
a plurality of port attachments molded as a continuous piece with the calibration port and the filter assembly, each port attachment being coupled to the calibration port and extending radially to the filter assembly;
a calibration hose having a first end coupled to the calibration port; and
a calibration fitting coupled to a second end of the calibration hose, the calibration fitting being mounted relative to the detachable filter assembly, wherein the calibration fitting is mounted to the attachment mechanism.

2. The detachable filter assembly of claim 1, wherein the fluid pathway is substantially enclosed.

3. The detachable filter assembly of claim 1, wherein the body comprises open sensor detection areas configured to provide fluid access to a sensing element.

4. The detachable filter assembly of claim 1, wherein the sensor module includes a guide that positions the sensor module into a correct installation configuration.

5. The detachable filter assembly of claim 1, wherein the calibration port comprises coupling mechanisms configured to secure a calibration hose to the calibration port.

6. The detachable filter assembly of claim 1, wherein the calibration port is at an offset angle relative to the sensor installation.

7. The detachable filter assembly of claim 1, wherein the plurality of port attachments are equally spaced radially from one another.

8. The detachable filter assembly of claim 7, wherein the plurality of port attachments comprise at least four port attachments.

9. The detachable filter assembly of claim 1, and further comprising a processor configured to compare a sensor-related output to a pre-set threshold for calibration.

10. The detachable filter assembly of claim 1, and further comprising a processor configured to compare a sensor-related output to a pre-set threshold for determining accuracy.

11. The detachable filter assembly of claim 1, and further comprising a processor configured to compare a sensor-related output to a pre-set threshold for determining whether an adjustment to process flow is required.

12. The detachable filter assembly of claim 1, wherein a calibration fluid is selectably caused to flow through the calibration hose by opening a gas cylinder coupled to the calibration hose.

13. The detachable filter assembly of claim 1, wherein a calibration fluid is selectably caused to flow through the calibration hose by an automated control system.

14. The detachable filter assembly of claim 13, wherein the calibration fluid is selectably caused to flow through the calibration hose automatically.

15. The detachable filter assembly of claim 1, wherein the attachment mechanism is a clamp.

* * * * *